United States Patent [19]

Flaherty et al.

[11] 4,193,306
[45] Mar. 18, 1980

[54] ULTRASONIC TESTING SYSTEM

[75] Inventors: John J. Flaherty, Elk Grove Village; Eric J. Strauts, Park Ridge, both of Ill.

[73] Assignee: Magnaflux Corporation, Chicago, Ill.

[21] Appl. No.: 952,844

[22] Filed: Oct. 19, 1978

[51] Int. Cl.² .......................................... G01N 29/04
[52] U.S. Cl. ...................................................... 73/629
[58] Field of Search ............... 73/609, 610, 611, 614, 73/615, 620, 622, 627, 629

[56] References Cited

U.S. PATENT DOCUMENTS

| 3,534,590 | 10/1970 | Kent et al. ............................ 73/622 |
| 4,088,030 | 5/1978 | Iversen et al. ......................... 73/629 |
| 4,111,053 | 9/1978 | Geithman et al. ...................... 73/609 |

Primary Examiner—Stephen A. Kreitman
Attorney, Agent, or Firm—Van Metre Lund

[57] ABSTRACT

An ultrasonic system for detection of defects is provided including a pulse-echo instrument having a cathode ray tube on which an A-scan visual indication of flaws is produced and including a doppler circuit arranged to produce a doppler signal in an audible range in response to movement of a transducer relative to defects in a pipe seam or other region being investigated. The doppler signal is applied to earphones, permitting the existence of defects to be reliably determined audibly, after which the defects may be more carefully studied through the visual indications on the cathode ray tube. The doppler signal is also recorded on one track of a magnetic tape with operator's comments being recorded on a second track of the same tape. The doppler circuit includes an oscillator operated during a gating time interval to generate a reference signal, a phase detector responsive to a reference signal and to echo ignals, and a sample and hold circuit for storing the output of the phase detector from one cycle to the next.

10 Claims, 5 Drawing Figures

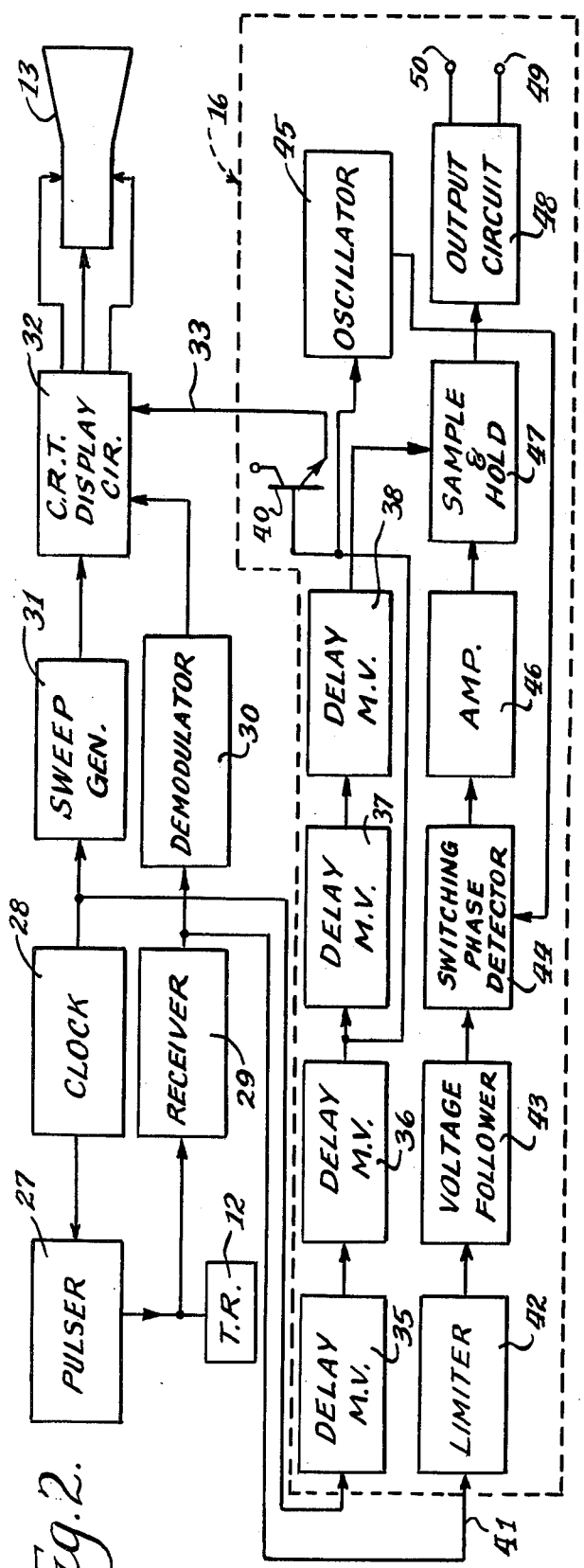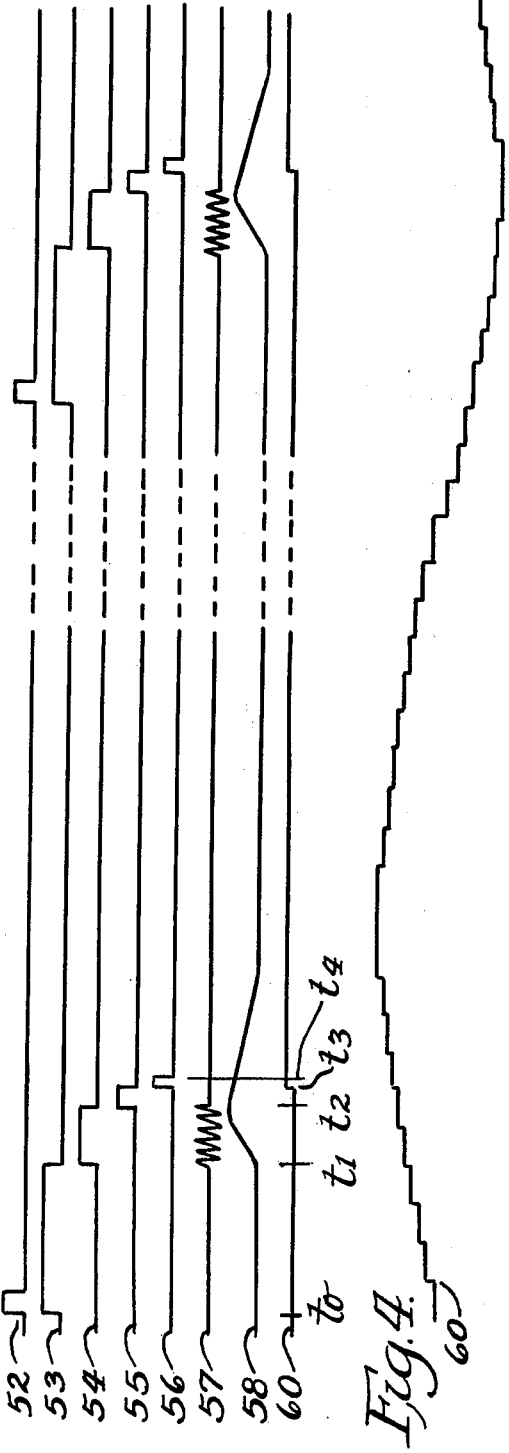

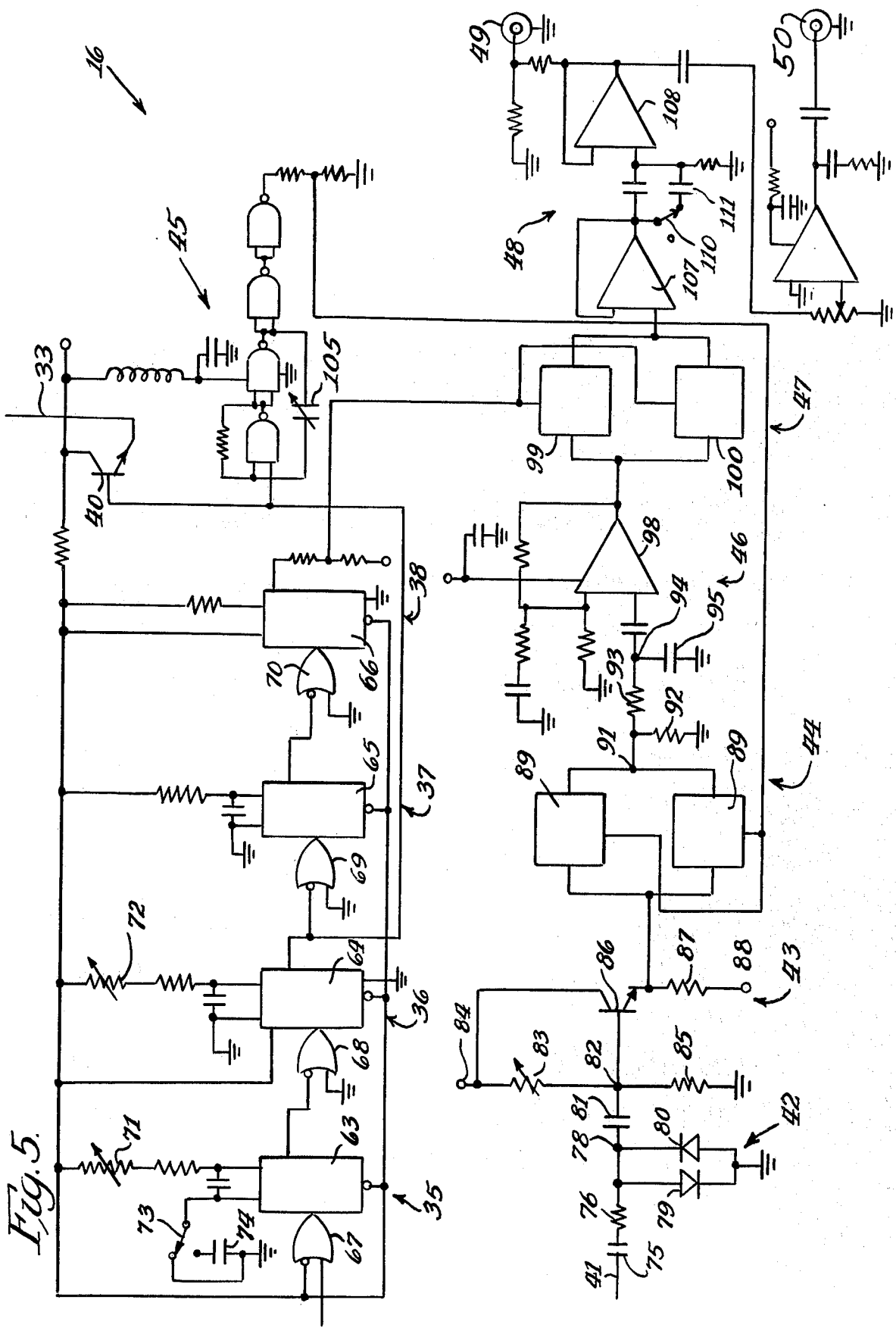

ULTRASONIC TESTING SYSTEM

This invention relates to an ultrasonic testing system and more particularly to the system which greatly increases the reliability of inspection of parts for defects while minimizing operator fatigue. The system also provides a permanent record for an inspection operation for review when desired. The required circuitry and equipment is relatively simple in construction and operation and economically manufacturable.

BACKGROUND OF THE PRIOR ART

In the typical ultrasonic system such as used for inspection of metal parts to detect internal defects therein, bursts of ultrasonic energy are transmitted from a transducer into a part while a horizontal sweep signal is applied to a cathode ray tube, with echo signals being effective to produce vertical deflections or "pips" on the screen of the cathode ray tube, a "A" scan arrangement being used. In many inspection operations, it is very difficult for the inspector to keep his attention and concentration and avoid fatigue. In the inspection of welded seams of pipe, it has been found that it helps to move the transducer toward and away from the weld zone with a "scrubbing" action, the result being movement of the echo indications which is easier to detect visually than stationary indications. Even so, however, the inspector must use a great deal of concentration and attention to avoid missing of defects and potential defects during the inspection operation.

SUMMARY OF THE INVENTION

This invention was evolved with the general object of overcoming disadvantages of prior ultrasonic testing systems and of improving the accuracy and reliability of the inspection of parts for defects. In accordance with this invention, an ultrasonic pulse-echo instrument is provided in which transducer means are energized to transmit a burst of ultrasonic energy into a part with echo signals being developed from the transducer means in response to reflections from defects within the part. The transducer means are arranged for back and forth movement toward and away from a defect to obtain a variable length wave transmission path between the transducer means and the defect. Doppler circuit means are provided for responding to changes in the timing of echo signals relative to the transmitted bursts and for developing a doppler signal at an audible frequency proportional to the rate of change in the effective length of the variable length transmission path, the doppler signal being applied to earphones or other electro-acoustical transducer means so as to produce an audible signal. With this arrangement, defects are easily and reliable detected and the arrangement does not require the concentrated attention required in systems in which only a visual indication is produced. The system, however, preferably, includes means for producing a visual indication of the position and size of a defect to obtain a closer study and more accurate indication of defects detected through the use of the doppler circuit arrangement.

An important feature of the invention is in the provision of recorder means for recording the doppler signal, the recorder means preferably being a tape recorder having one channel for recording of the doppler signal on one track of a tape and having a second channel for recording of comments of the operator or inspector on a second track of the tape. A permanent record is obtained as to the testing of each part and the recording may be used for monitoring the performance of inspectors.

Important specific features relate to the doppler circuit means which preferably comprises phase detector means for comparing the echo signals with a reference signal, the reference signal having a certain frequency and having a substantially fixed phase relationship to the transmitted bursts. Preferably the frequency of the reference signal is approximately the same as the resonant frequency of the transducer means.

According to a further feature an oscillator is provided for generating the reference signal, the oscillator being energized by gating means during a certain gating time interval following the transmission of each burst of ultrasonic energy. The signal is thereby in fixed phase relationship to the transmitted bursts with a coherent relationship.

Another specific feature relates to the provision of a sample and hold circuit so operated as to produce a doppler signal of large amplitude without requiring a high gain amplifier.

This invention contemplate other objects, features and advantages which will become more fully apparent from the following detailed description taken with the accompanying drawings.

BRIEF DESCRIPTION OF THE DRAWINGS

FIG. 2 is a block diagram of an instrument of the system of FIG. 1 with a doppler module connected thereto, in accordance with the invention;

FIG. 3 illustrates waveforms produced at certain points of the circuitry shown in FIG. 2;

FIG. 4 also illustrates waveforms produced at certain points, on a time base which is greatly compressed in relation to that of FIG. 3; and FIG. 5 is a circuit diagram of the doppler module illustrated in block form in FIG. 2.

DESCRIPTION OF A PREFERRED EMBODIMENT

Figure 1:
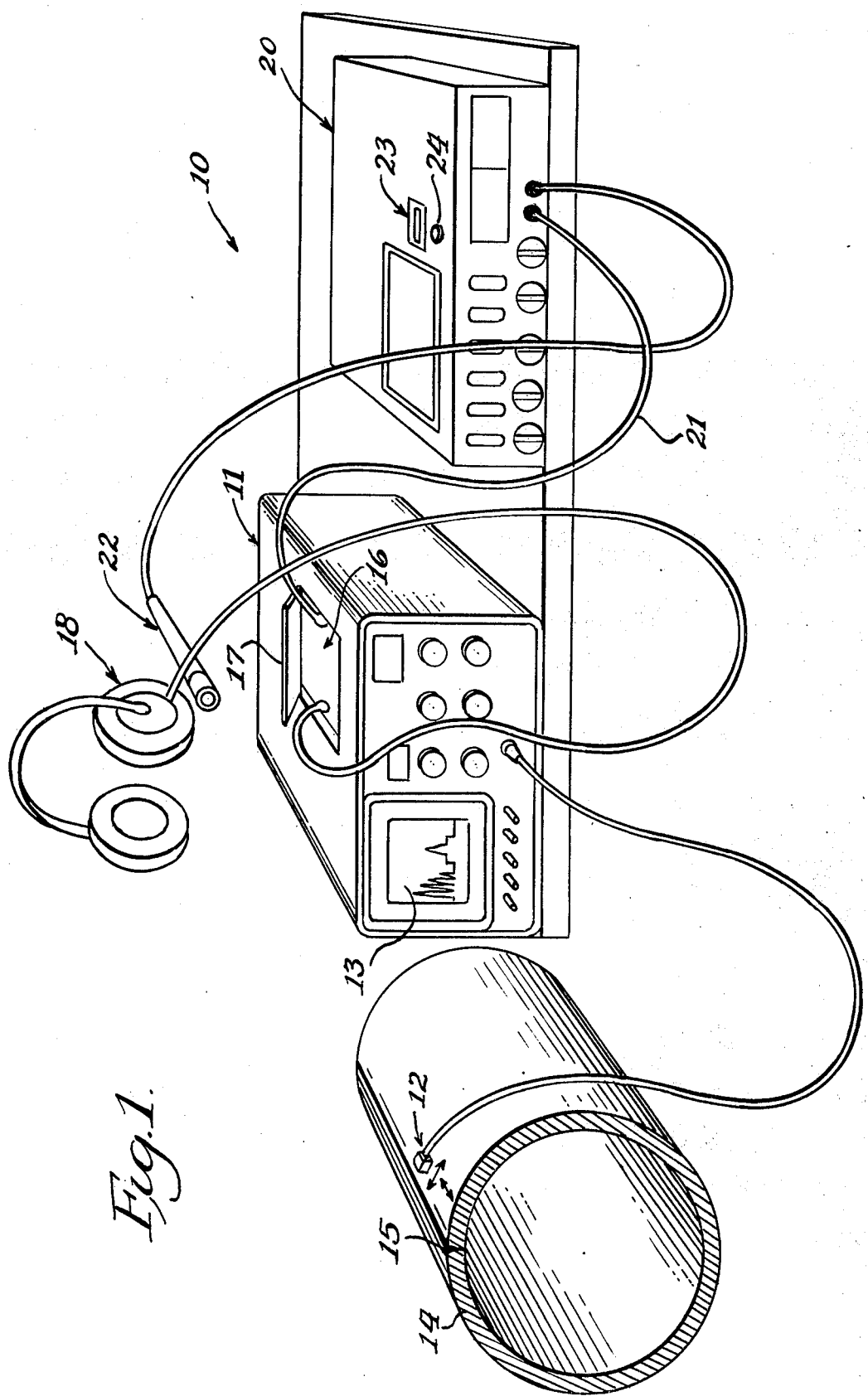
FIG. 1 is a perspective view illustrating an ultrasonic testing system constructed in accordance with the invention.

Reference numeral 10 generally designates an ultrasonic testing system constructed in accordance with the principles of this invention. The illustrated system 10 includes a portable test instrument 11 which is connected to a transducer 12 and which includes a cathode ray tube 13 having a screen on which visual indications are produced. Transducer 12 is shown disposed on the surface of a pipe 14 for inspection of a welded seam 15 of the pipe 14. The transducer 12 is energized periodically to transmit a burst of ultrasonic waves into the pipe, the transducer 12 being arranged to transmit at an angle such that shear waves travel to the seam 15 to be reflected back by discontinuities therein. The transducer produces echo signals in response to reflections back from discontinuies in the seam.

A pulse-echo A-scan indication is produced on the screen of the cathode ray tube 13, vertical deflections or "pips" being produced in response to the echo signals.

In normal operation, the operator moves the transducer 12 along the length of the pipe parallel to the seam 15 while observing the screen of the cathode ray tube 13. He may also move the transducer 12 toward and away from the seam 15, with a "scrubbing" action such as to produce a corresponding horizontal movement of pips developed from flaws in the seam 15. Moving pips are usually easier to detect visually but concentrated attention is required when flaws are to be reliably detected solely from visual observation of the cathode ray tube screen.

In accordance with this invention, doppler circuit means are provided for producing a signal in a low frequency audible range and in response to movement of the transducer toward and away from defects. In the illustrated system, such doppler circuit means are incorporated in a module which is adapted to be plugged into a well in the top of the instrument 11, below a door 17. The module 16 includes a connection for earphones 18, permitting the operator to listen to audible signals generated by transducer movements. In addition, the module 16 includes an adjustable gating arrangement permitting the audible signals to be generated from signals received from within only a selected distance range.

In operation, the operator places the transducer 12 on the pipe 14, or other part to be inspected, and by observing the screen of the cathode ray tube 13 and listening to sounds produced by the earphones 18, he can determine the optimum spacing between the transducer 12 and the seam 15 and the optimum adjustment of the distance gate. He then slowly moves the transducer 12 in an axial direction relative to the pipe 14 while rapidly moving it toward and away from the seam 15 with the scrubbing action described above. When the seam is satisfactory, the operator will hear through the earphones 18 only a relatively low intensity "swishing" type of sound generated from minor variations in the character of the metallic structure of the pipe. However, when the transducer 12 is moved opposite a crack or other inhomogeneity of significant size, a sound of much higher intensity is heard having a frequency related to the velocity of movement of the transducer 12 toward and away from the crack.

When the operator hears such a signal, he may then make a very careful inspection of the region and adjust the transducer 12 in a manner such as to maximize the height of the pip produced on the screen and he can then carefully note the position and orientation of the crack and the height of the pip.

Another important feature of the invention is in the provision of means for recording the signals produced by the module 16 along with comments of the inspector. As illustrated, a stereo or dual channel cassette type tape recorder 20 is provided having an input jack for one channel connected through a cord 21 to the signal output of the module 16 and having an input jack for the other channel connected to a microphone 22. The recorder 20 may also include a tape counter 23 which is resettable by a button 24. As the inspector inspects the part, he can identify and describe the part being inspected and the visual indications produced and locations, etc. Thus, for example, he may begin to test a particular pipe saying "Now starting test of weld of pipe marked number 32." When he discovers a defect he may say, "Flaw noted at a distance of four feet, three inches from end of pipe, oriented parallel to axis of pipe, pip height of 2.6 centimeters." He may also make a written record identifying the pipe, the tape cassette and the readings of the tape counter at the beginning and end of the test and at points where indications of interest are observed.

In this way, a permanent record is obtained as to the testing operation. By listening to the recording, the performance of the inspector can be verified at a later time and it is possible to review the performance of inspectors to insure that the testing operations are being properly carried out.

The arrangement also reduces boredom of inspectors, giving them tasks to perform other than simply trying to keep concentrated attention on visual observation of a cathode ray tube screen and further increases the reliability of a testing operation.

FIG. 2 is a block diagram illustrating circuitry of the instrument 10 and of the doppler circuit module 16. The transducer 12 is coupled to the output of a pulser 27 which is operated at a certain repetition rate in response to signals from a clock 28. The transducer 12 is also coupled to the input of an RF amplifier or receiver 29 the output of which is applied to a demodulator 30. A sweep generator 31, controlled from the clock 28, applies a horizontal deflection signal through display circuitry 32 to the cathode ray tube 13 and a video signal from the demodulator 30 is also applies through the circuitry 32 to the cathode ray tube 13 for vertical deflection of the splat on the screen of the tube, a typical A-scan arrangement being used.

In addition to sweep and video signals, a gate position signal is applied from the module 16 through a line 33 and through the display circuitry 32 to the cathode ray tube 13. The gate position signal is developed during a certain time interval which is delayed relative to the start of each sweep, to cause vertical deflection and to indicate visually the signals which are processed in the module 16 as hereinafter described. The start and duration of the gate position signal are adjustable by the operator to select the region within the part which is to be inspected for flaws.

The module 16 includes four delay multivibrators 35-38 connected in cascade. The first multivibrator 35 is triggered in synchronized relation to the pulsing of the transducer by a signal applied through line 39 from the clock 28. The multivibrator 35 develops an output signal for a certain time interval, which is adjustable, and at the end thereof, the multivibrator 36 is triggered to develop an output signal for another certain time interval which is also adjustable. The output of the second multivibrator 36 is applied through a driver transistor 40 to the line 33 to apply the position gate signal to the display circuit 32, the start of the gate signal being determined by the multivibrator 35 and its duration being determined by the multivibrator 36. With regard to the delay multivibrators 37 and 38, such operate to develop a pulse for control of a sample and hold circuit as hereinafter described.

An RF signal from the output of the receiver 29 is applied through a line 41 and through a limiter circuit 42 and a voltage-follower circuit 43 to a switching phase detector 44 to which a reference RF signal is applied from a gated oscillator 45. The oscillator 45 is controlled from the output of the multivibrator 36 and operates for the duration of the position gate signal to develop an RF signal which during successive cycles of operation has a stable time relationship to the pulsing of the transducer 12. The frequency of the signal developed by the oscillator 45 is preferably close to the resonant frequency of the transducer 12, but need not be precisely the same.

During each position gate interval, each echo signal produced at the output of receiver 29 and applied through limiter circuit 42 and voltage-follower 43 to the switching phase detector 44 has a certain time relationship to the reference signal applied from oscillator 45 to the phase detector 44 and the phase detector develops a certain output signal. If the echo signal is produced from an inhomogeneity within the part and if the transducer is in motion, a doppler effect is produced such that the phase or time relationship of the signals applied to the phase detector 44 changes from one cycle to the next and the amplitude of the signal produced at the output of the phase detector 44 varies at a low frequency which is proportional to the velocity of movement.

The amplitude of the output of the phase detector 44 does not change in response to echoes from a defect when there is no movement of the transducer 12 relative to the defect. Random noise signals produce minimal generation of signals at the low frequency rate since they tend to cancel out over any substantial number of cycles. Accordingly, the arrangement is insensitive to noise signals but is highly sensitive to motion signals.

The output of the switching phase detector 44 is applied through an amplifier 46 to a sample and hold circuit 47 to which a control pulse is applied during each cycle from the output of the multivibrator 38. The control pulse developed by the multivibrator 38 starts after the end of the position gate signal with a delay determined by the multivibrator 37 and the control pulse has a duration determined by the multivibrator 38. At the end of each position gate signal, the output of the phase detector 44 is at a certain level which is amplified by the amplifier 46 and when after a certain delay, the control pulse is applied from multivibrator 38 to the sample and hold circuit 47, the output of the sample and hold circuit 47 is established at a corresponding level and remains at such level until the next cycle.

The output of the sample and hold circuit 47 is applied to an output circuit 48 which supplies signals in the audio frequency range to jacks 49 and 50 for connection to headphones 18 and recorder 20.

The operation may be more readily understood with reference to the timing diagrams of FIGS. 3 and 4. In FIG. 3, reference numeral 52 designates the waveform of the clock signal applied to the input of multivibrator 35, consisting of periodic pulses synchronized with pulses applied to the transducer 12.

Reference numeral 53 indicates the waveform at the output of multivibrator 35 which consists of pulses which start with the clock pulses at a time $t_0$ and in at a time $t_1$, after an adjustable time interval.

Reference numeral 54 indicates the waveform at the output of multivibrator 36 which consists of pulses starting at time $t_1$ and ending at time $t_2$, the time from $t_1$ to $t_2$ being the gating time interval.

Reference numeral 55 indicates the waveform at the output of multivibrator 37 which consists of pulses starting at time $t_2$ and ending at time $t_3$.

Reference numeral 56 indicates the waveform at the output of multivibrator 38 consisting of pulses of short duration starting at time $t_3$ and ending at time $t_4$, such pulses being applied to the sample and hold circuit 47. Reference numeral 57 indicates the waveform at the output of the oscillator 45 developed during the position gating time interval $t_1$-$t_2$.

Reference numeral 58 indicates a type of waveform which may be produced at the output of the switching phase detector 44, in the form of a signal which increases in amplitude during the time interval $t_1$-$t_2$ and then decays in amplitude.

Reference numeral 60 indicates the waveform at the output of the sample and hold circuit 47, of one amplitude during one cycle and of a different amplitude in the following cycle, such as obtained with relative motion between the transducer 12 and a defect. In FIG. 4, the same waveform 60 is shown on a greatly compressed time base to show a large number of cycles of operation and to show how a cycle of a low frequency signal is produced in response to movement of the transducer.

It is noted that the output of the switching phase detector 44 could be applied to a conventional type of integrating circuit to produce a signal which could be applied to a conventional amplifier to produce the doppler signal, eliminating the sample and hold circuit 47 and associated circuitry. However, the signal produced at the output of the integrating circuit in such an arrangement would be of very low amplitude, requiring a high degree of amplification, since the time duration of each echo signal is a very small fraction of the total time for each cycle. With the arrangement is illustrated, using the sample and hold circuit, a large amplitude output signal can be more readily produced and without instability and other problems associated with high gain amplifiers.

Referring to FIG. 5, the delay multivibrator circuits 35-38 comprise integrated circuits 63-66 connected in circuit with gate circuits 67-70 and resistor and capacitor components in the manner as shown, including variable resistances 71 and 72 which are adjustable to control the time duration of operation of the multivibrators 35 and 36 to thereby control the position and width of the gate. A switch 73 is provided, connected in circuit with a capacitor 74 to control the position range. The components of the multivibrators 37 and 38 are fixed in the illustrated circuit, but might be adjustable if desired.

In the limiter circuit 42, the line 41 is connected through a capacitor 75 and a resistor 76 to a circuit point 78 which is connected to ground through a pair of diodes 79 and 80, to limit the amplitude of the signal developed at the circuit point 78.

The circuit point 78 of the limiter circuit 42 is connected through a capacitor 81 to a circuit point 82 which is connected through an adjustable resistor 83 to a power supply terminal 84, through a resistor 85 to ground and directly to the base of a transistor 86. The collector of the transistor 86 is connected to the power supply terminal 84 and the emitter thereof is connected through a resistor 87 to a negative power supply terminal 88.

The resistor 83 is adjustable to adjust the level, preferably to obtain a bi-directional signal at the emitter of the transistor 86 which forms the output of the voltage-limiter circuit 43.

The switching phase detector 44 comprises a pair of bilateral switch devices 89 and 90 connected as shown and to a circuit point 91 which is connected through a resistor 92 to ground and which is connected through a resistor 93 to a circuit point 94 connected through a capacitor 95 to ground. The resistor 93 and capacitor 95 may provide a time constant which is of generally the same order of magnitude of the duration of the gating time interval. The amplifier 46 includes an operational amplifier 98 connected in circuit with resistors and capacitors as shown in the drawings.

The sample and hold circuit 47 is like the switching phase detector 44, comprising a pair of bilateral switch devices 99 and 100.

The oscillator 45 comprises four gate circuits connected in circuit with resistor, capacitor and inductor components as shown, including a variable capacitor 105 which adjusts the frequency of operation. As noted above, the frequency of operation is preferably approximately equal to the resonant frequency of the transducer but need not be precisely the same, especially if the transducer is highly damped with little "ringing" operation. If the transducer does ring to a substantial extent, the frequency of the oscillator should be matched thereto as closely as possible to obtain maximum advantage from the ringing operation.

The output circuit 48 includes integrated circuits 107, 108 and 109 connected in circuit with resistors and capacitors in the manner as shown. A switch 110 is connected in circuit with a capacitor 111 to provide a selective degree of filtering and a potentiometer 112 is provided, operative to provide a control of the volume produced in the earphones 18.

It will be understood that modification and variations may be effected without departing from the spirit and scope of the novel concepts of this invention.

We claim as our invention:

1. In an ultrasonic pulse-echo instrument for detection of defects in a solid part, transducer means, transmitting and receiving means for energizing said transducer means to transmit a burst of ultrasonic energy into the part and for developing echo signals in response to reflections from defects within the part, said transducer means being arranged for back and forth movement toward and away from a defect to obtain a variable length wave transmission path between said transducer means and the defect, doppler circuit means coupled to said transmitting and receiving means for responding to changes in the timing of said echo signals relative to the transmitted bursts and for developing a doppler signal at an audible frequency proportional to the rate of change in the effective length of said variable length wave transmission path, and means for applying said doppler signal to electro-acoustical transducer means to produce an audible signal in response to said movement of said transducer means toward and away from the defect.

2. In an instrument as defined in claim 1, means for producing a visual indication of the position and size of a defect, comprising: a cathode ray tube having a screen, sweep means coupled to said cathode ray tube for producing deflection in one direction and means responsive to said echo signals to produce deflection in a transverse direction.

3. In an instrument defined in claim 2, recorder means for recording said doppler signal.

4. In an instrument as defined in claim 3, said recorder means being a tape recorder having one channel for recording of said doppler signal on one track of a tape and having a second channel for recording of a signal on a second track of the tape, and a microphone coupled to said second channel for recording comments of the operator of the instrument of said second track of the tape.

5. In an instrument as defined in claim 1, gating means associated with said doppler circuit means and arranged for producing a response only to echo signals received from defects within a limited distance range.

6. In an instrument as defined in claim 1, said doppler circuit means comprising reference signal generator means for generating a reference signal having a certain frequency and having a substantially fixed phase relationship with respect to transmitted bursts, and phase detector means for comparing said reference signal and said echo signals.

7. In an instrument as defined in claim 6, wherein said transducer means has a certain resonant frequency, said frequency of said reference signal being approximately the same as said resonant frequency.

8. In an instrument as defined in claim 6, said reference signal generator means comprising an oscillator.

9. In an instrument as defined in claim 8, gating means for energizing said oscillator during a certain gating time interval following the transmission of each burst of ultrasonic energy.

10. In an instrument as defined in claim 9, said gating means comprising a first delay multivibrator triggered in synchronism with the transmission of said bursts of ultrasonic energy to operate for a certain time interval, and a second delay multivibrator triggered from said first delay multivibrator to operate for the gating time interval, and means for adjusting said time intervals.

* * * * *